US011950869B2

(12) United States Patent
Hazelton et al.

(10) Patent No.: US 11,950,869 B2
(45) Date of Patent: Apr. 9, 2024

(54) SYSTEM AND METHOD FOR PROVIDING ON-DEMAND FUNCTIONALITY DURING A MEDICAL PROCEDURE

(71) Applicant: INTUITIVE SURGICAL OPERATIONS, INC., Sunnyvale, CA (US)

(72) Inventors: Andrew J. Hazelton, San Carlos, CA (US); Kayla Keifer Anderson, Campbell, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 597 days.

(21) Appl. No.: 16/117,821

(22) Filed: Aug. 30, 2018

(65) Prior Publication Data

US 2019/0060014 A1 Feb. 28, 2019

Related U.S. Application Data

(60) Provisional application No. 62/552,271, filed on Aug. 30, 2017.

(51) Int. Cl.
*A61B 34/35* (2016.01)
*A61B 1/00* (2006.01)
(Continued)

(52) U.S. Cl.
CPC .......... *A61B 34/35* (2016.02); *A61B 1/00147* (2013.01); *A61B 1/05* (2013.01);
(Continued)

(58) Field of Classification Search
CPC .............. A61B 34/73; A61B 2034/731; A61B 1/00112; A61B 1/06; A61B 1/0661;
(Continued)

(56) References Cited

U.S. PATENT DOCUMENTS 2,793,639 A * 5/1957 Roberge ................... A61B 1/31
600/178
5,431,670 A * 7/1995 Holmes ................ A61B 17/062
606/147

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Anh Tuan T Nguyen
*Assistant Examiner* — Shankar Raj Ghimire
(74) *Attorney, Agent, or Firm* — Haynes & Boone, LLP (57) ABSTRACT

A system for providing on-demand functionality during a medical procedure includes an instrument, an accessory, and a mounting device attached to one or more of the instrument and the accessory. The instrument includes an instrument body and an end effector. The end effector providing a first functionality. The accessory providing a second functionality. The mounting device removably couples the accessory to the instrument to augment the first functionality with the second functionality. In one example, the end effector includes jaws to provide a surgical functionality, and the first accessory includes a camera to provide a complementary monitoring functionality. In another example, the mounting device includes a mechanical mechanism and/or a magnetic mechanism for removably coupling the accessory to the instrument.

20 Claims, 6 Drawing Sheets

(51) Int. Cl.
| | | |
|---|---|---|
| *A61B 1/05* | (2006.01) | |
| *A61B 5/055* | (2006.01) | |
| *A61B 17/00* | (2006.01) | |
| *A61B 17/29* | (2006.01) | |
| *A61B 34/00* | (2016.01) | |
| *A61B 90/00* | (2016.01) | |
| *A61B 90/57* | (2016.01) | |
| *A61B 34/20* | (2016.01) | |
| *A61B 34/30* | (2016.01) | |
| *A61B 90/30* | (2016.01) | |
| *A61B 90/50* | (2016.01) | |
| *G16H 20/40* | (2018.01) | |
| *G16H 40/63* | (2018.01) | |
| *G16H 40/67* | (2018.01) | |

(52) U.S. Cl.
CPC ........ *A61B 5/055* (2013.01); *A61B 17/00234* (2013.01); *A61B 17/29* (2013.01); *A61B 34/25* (2016.02); *A61B 34/74* (2016.02); *A61B 90/37* (2016.02); *A61B 2017/00353* (2013.01); *A61B 2017/00477* (2013.01); *A61B 2017/00876* (2013.01); *A61B 34/20* (2016.02); *A61B 2034/252* (2016.02); *A61B 2034/305* (2016.02); *A61B 2034/741* (2016.02); *A61B 2034/742* (2016.02); *A61B 2090/306* (2016.02); *A61B 90/361* (2016.02); *A61B 2090/371* (2016.02); *A61B 2090/3735* (2016.02); *A61B 2090/378* (2016.02); *A61B 90/50* (2016.02); *A61B 90/57* (2016.02); *G16H 20/40* (2018.01); *G16H 40/63* (2018.01); *G16H 40/67* (2018.01)

(58) Field of Classification Search
CPC ........... A61B 2017/00292; A61B 2017/00296; A61B 1/00087; A61B 1/00089; A61B 1/00121; A61B 1/00131; A61B 1/0014; A61B 17/295; A61B 34/35; A61B 1/00147; A61B 17/29; A61B 1/05; A61B 34/25; A61B 17/00234; A61B 34/74; A61B 90/37; A61B 5/055; A61B 2090/306; A61B 90/361; A61B 2017/00477; A61B 2017/00353; A61B 2090/371; A61B 2090/3735; A61B 2017/00876; A61B 2090/378; A61B 90/57; A61B 34/20; A61B 2034/742; A61B 2034/741; A61B 90/50; A61B 2034/305; A61B 2034/252; A61B 34/30; A61B 1/00149; A61B 1/005; A61B 1/012; A61B 1/313; A61B 90/30; G02B 23/2461; G02B 21/0012; G16H 20/40; G16H 40/67; G16H 40/63
See application file for complete search history.

(56) References Cited

U.S. PATENT DOCUMENTS

| | | | | |
|---|---|---|---|---|
| 5,489,256 | A * | 2/1996 | Adair | A61B 1/00073 |
| | | | | 600/123 |
| 5,615,920 | A * | 4/1997 | O'Kane | F21V 33/008 |
| | | | | 294/65.5 |
| 8,267,854 | B2 * | 9/2012 | Asada | A61B 1/0005 |
| | | | | 600/114 |
| 10,123,821 | B2 * | 11/2018 | Ibrahim | A61B 17/3421 |
| 2007/0255100 | A1 * | 11/2007 | Barlow | A61B 1/3132 |
| | | | | 600/114 |
| 2008/0208006 | A1 * | 8/2008 | Farr | A61B 1/0684 |
| | | | | 600/178 |
| 2008/0300458 | A1 * | 12/2008 | Kim | A61B 34/73 |
| | | | | 600/118 |
| 2009/0163943 | A1 * | 6/2009 | Cavanaugh | A61B 17/50 |
| | | | | 606/180 |
| 2009/0187072 | A1 * | 7/2009 | Manohara | A61B 1/045 |
| | | | | 600/109 |
| 2010/0125165 | A1 * | 5/2010 | Torii | A61B 1/00045 |
| | | | | 600/106 |
| 2011/0208011 | A1 * | 8/2011 | Ben-Horin | A61B 1/00156 |
| | | | | 600/300 |
| 2012/0053406 | A1 * | 3/2012 | Conlon | A61B 17/29 |
| | | | | 606/49 |
| 2012/0088965 | A1 * | 4/2012 | Stokes | A61B 1/05 |
| | | | | 600/104 |
| 2012/0108900 | A1 * | 5/2012 | Viola | A61B 1/053 |
| | | | | 600/109 |
| 2014/0343358 | A1 * | 11/2014 | Hameed | G02B 23/2423 |
| | | | | 600/109 |
| 2015/0265143 | A1 * | 9/2015 | Yoon | A61B 90/37 |
| | | | | 600/104 |
| 2016/0015255 | A1 * | 1/2016 | Dejima | A61B 1/00131 |
| | | | | 600/106 |
| 2016/0174814 | A1 * | 6/2016 | Igov | A61B 17/0218 |
| | | | | 600/106 |
| 2016/0235400 | A1 * | 8/2016 | Hiernaux | G02B 23/2476 |
| 2016/0331208 | A1 * | 11/2016 | Kikuchi | A61B 1/018 |
| 2017/0245745 | A1 * | 8/2017 | Ohara | A61B 1/0661 |
| 2018/0296289 | A1 * | 10/2018 | Rodriguez-Navarro | A61B 17/0218 |
| 2019/0350619 | A1 * | 11/2019 | Fujii | A61B 1/313 |

* cited by examiner

SYSTEM AND METHOD FOR PROVIDING ON-DEMAND FUNCTIONALITY DURING A MEDICAL PROCEDURE

CROSS-REFERENCE TO RELATED APPLICATIONS

This application claims the benefit of U.S. Provisional Application 62/552,271 filed Aug. 30, 2017, which is incorporated by reference herein in its entirety.

TECHNICAL FIELD

The present disclosure is directed to systems for performing a medical procedure and more particularly to a system for providing on-demand functionality during a medical procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

During the performance of a medical procedure, an operator employs one or more functionalities provided by one or more devices inserted into the patient body. For example, an end effector of a medical instrument may provide a first functionality, and a medical accessory may provide a second functionality. Whereas the end effector may be steerable by the operator from outside the body, the accessory may lack independent steering capabilities.

Accordingly, it would be desirable to use medical accessories to provide on-demand functionality during a medical procedure.

SUMMARY

The embodiments of the invention are best summarized by the claims that follow the description.

According to some embodiments, system for providing on-demand functionality during a medical procedure includes an instrument, an accessory, and a mounting device attached to one or more of the instrument and the accessory. The instrument includes an instrument body and an end effector. The end effector providing a first functionality. The accessory providing a second functionality. The mounting device removably couples the accessory to the instrument to augment the first functionality with the second functionality.

According to some embodiments, a medical apparatus includes a medical accessory and a mount. The medical accessory provides one or more first functionalities. The mount is used for removably coupling the medical accessory to a medical instrument without interfering with one or more second functionalities provided by the medical instrument.

According to some embodiments, a method includes inserting a medical instrument into a patient body, mounting an accessory to the medical instrument, and performing a medical procedure. The medical instrument includes an end effector that provides a first functionality. The accessory provides a second functionality. Performing the medical procedure includes using the first and second functionalities concurrently.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1A:
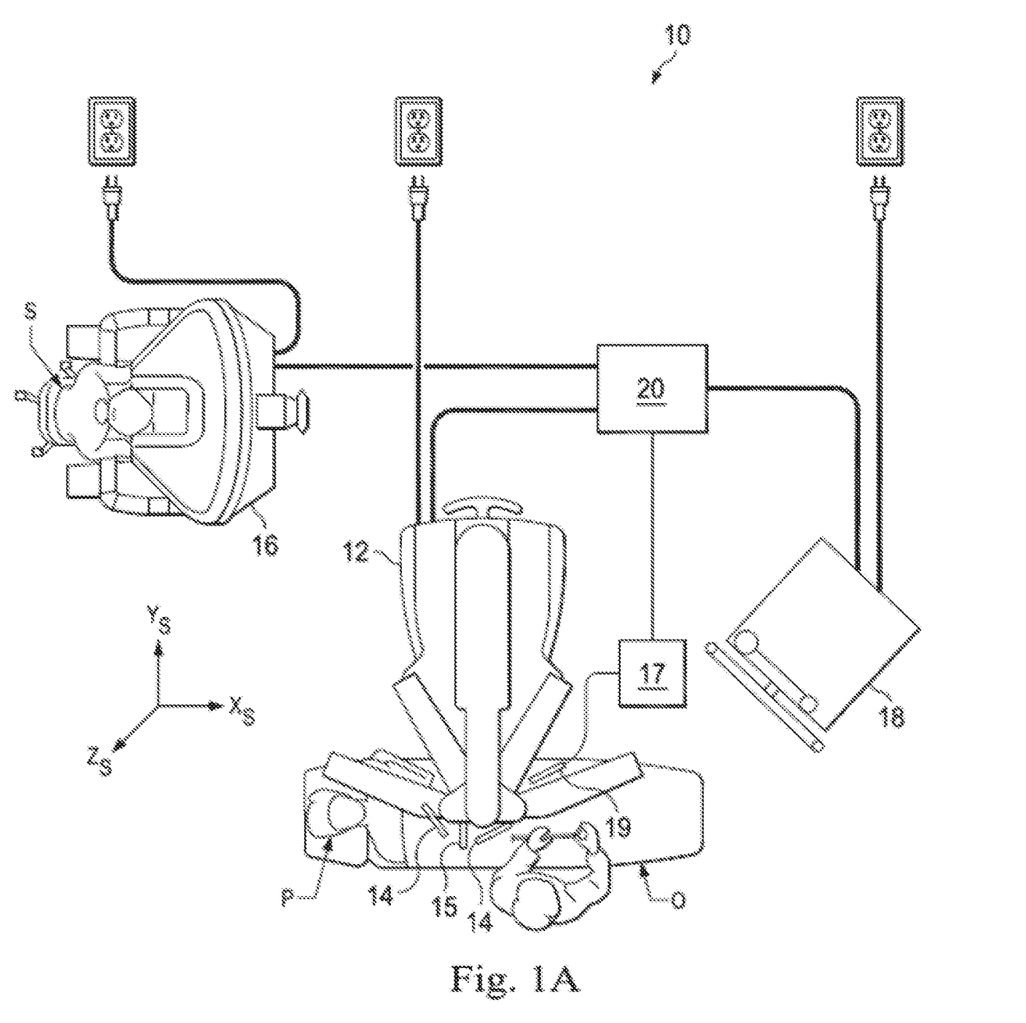
FIG. 1A is a schematic view of a teleoperated medical system in a surgical frame of reference, in accordance with an embodiment of the present disclosure.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, XS, YS, ZS. As will be described, the teleoperated medical systems of this disclosure are under the teleoperated control of a surgeon. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table O on which a patient P is positioned. The teleoperated assembly 12 may be referred to as a patient side cart. A medical instrument system 14 and an endoscopic imaging system 15 are operably coupled to the teleoperated assembly 12. An operator input system 16 allows a surgeon or other type of clinician S to view images of or representing the surgical site and to control the operation of the medical instrument system 14 and/or the endoscopic imaging system 15. A supplemental imaging system 17 including a minimally invasive image capture probe 19 may be used with the medical instrument system 14 and endoscopic imaging system 15 as will be described below. Together with the patient side cart, the supplemental imaging system 17 may be known as a patient side system. The endoscopic imaging system 15 provides images of the external surfaces of anatomic structures within the surgical environment. The supplemental imaging system 17 may be an internal imaging system such as an ultrasound, x-ray, or gamma imaging system capable of imaging beyond the external surface of the anatomical structures.

The operator input system 16 may be located at a surgeon's console, which is usually located in the same room as operating table O. It should be understood, however, that the surgeon S can be located in a different room or a completely different building from the patient P. The surgeon's console 16 includes left and right eye displays for presenting the surgeon S with a coordinated stereo view of the surgical site that enables depth perception. The console 16 further includes one or more input control devices which cause the teleoperated assembly 12 to manipulate one or more instruments or the endoscopic imaging system. The input control devices can provide the same degrees of freedom as their associated instruments 14 to provide the surgeon S with telepresence, or the perception that the input control devices are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperated assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperated assembly 12 may include a kinematic structure of one or more non-servo controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic system 15, the operator input system 16, and monitors on the electronics system 18. The control system 20 may also receive and process images from the supplemental imaging system 17. The electronics cart 18 may house components of the endoscopic imaging system 15, the supplemental imaging system 17, the control system 20 as well as monitors and processors for processing and displaying captured images.

The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperated assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator input system. The exact number of manipulator assemblies will depend on the surgical procedure and the space constraints within the operating room, among other factors. The operator input systems may be collocated, or they may be positioned in separate locations.

Figure 1B:
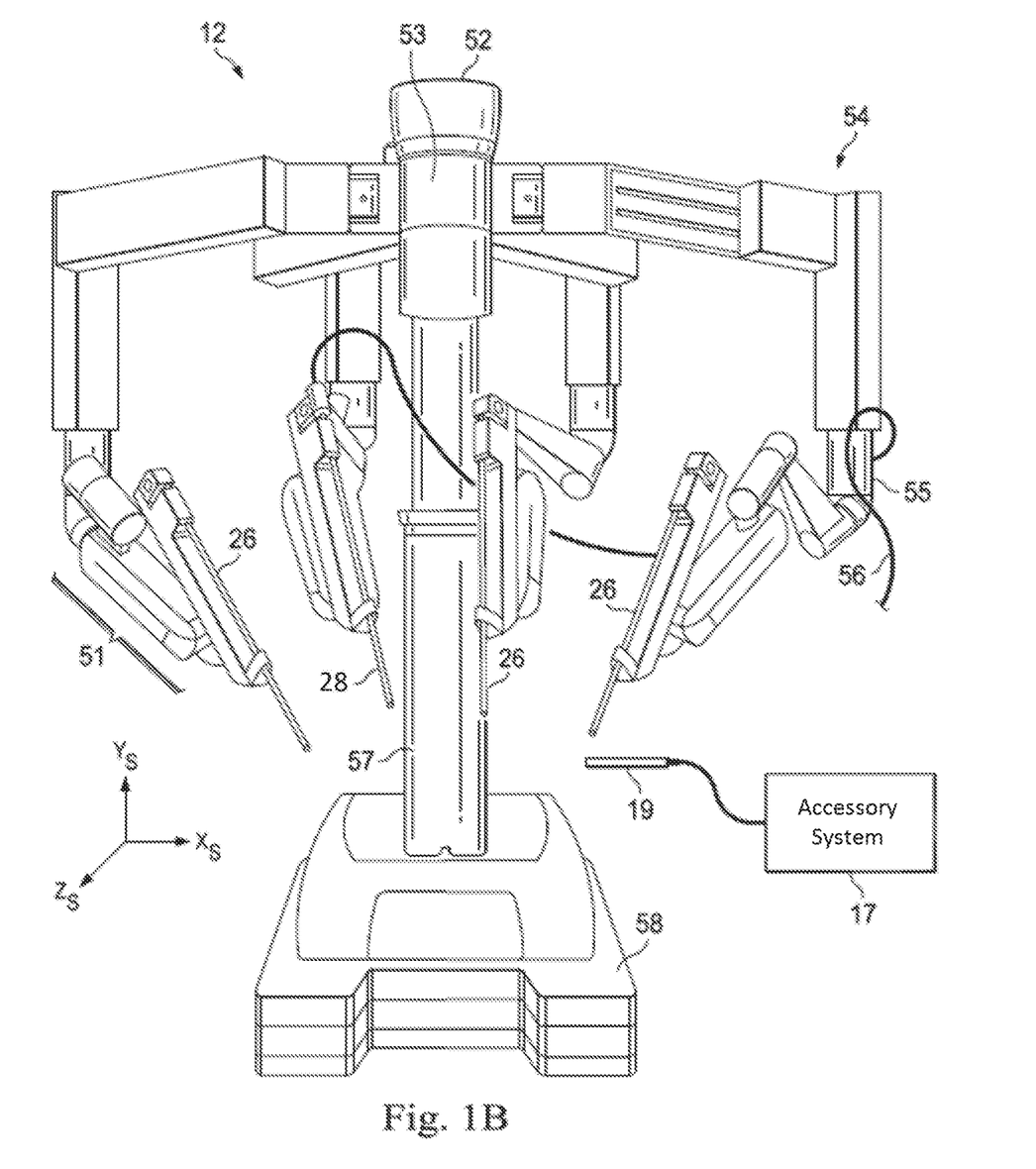
FIG. 1B is a perspective view of patient side systems, according to one example of principles described herein.

FIG. 1B is a perspective view of one embodiment of a teleoperated assembly 12 and an accessory system 17 which may, together, be referred to as a patient side system. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 12 may also include a telescoping horizontal cantilever 52 for moving the orienting platform 53 in a horizontal direction.

In the present example, each of the arms 54 connects to a manipulator arm 51. The manipulator arms 51 may connect directly to a surgical tools 26. The manipulator arms 51 may be teleoperable. In some examples, the arms 54 connecting to the orienting platform are not teleoperable. Rather, such arms 54 are positioned as desired before the surgeon begins operation with the teleoperative components.

Accessory system 17 may provide one or more functionalities that augment and/or complement the functionalities provided by surgical tools 26. Accessory system 17 includes an accessory 19 to provide the one or more additional functionalities. Accessory 17 may be a minimally invasive instrument sized for insertion into the surgical environment. Examples of accessories and their functionalities are discussed in greater detail below with reference to FIGS. 2A-6. Accessory 17 may include an endoscopic imaging system.

Endoscopic imaging systems (e.g., systems 15, 17, and/or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field of view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field of view of the patient anatomy. An endoscopic instrument may be a fully sterilizable assembly with the endoscope cable, handle and shaft all rigidly coupled and hermetically sealed.

Figure 2A:
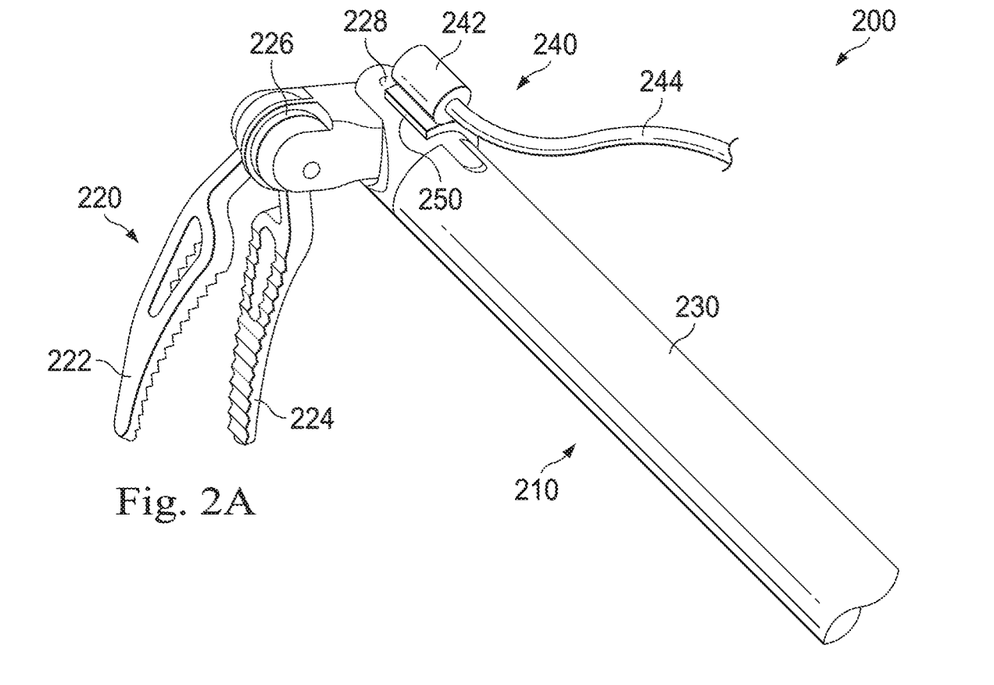
FIGS. 2A and 2B are simplified diagrams of a system for providing on-demand functionality during a medical procedure according to some embodiments.
Figure 2B:
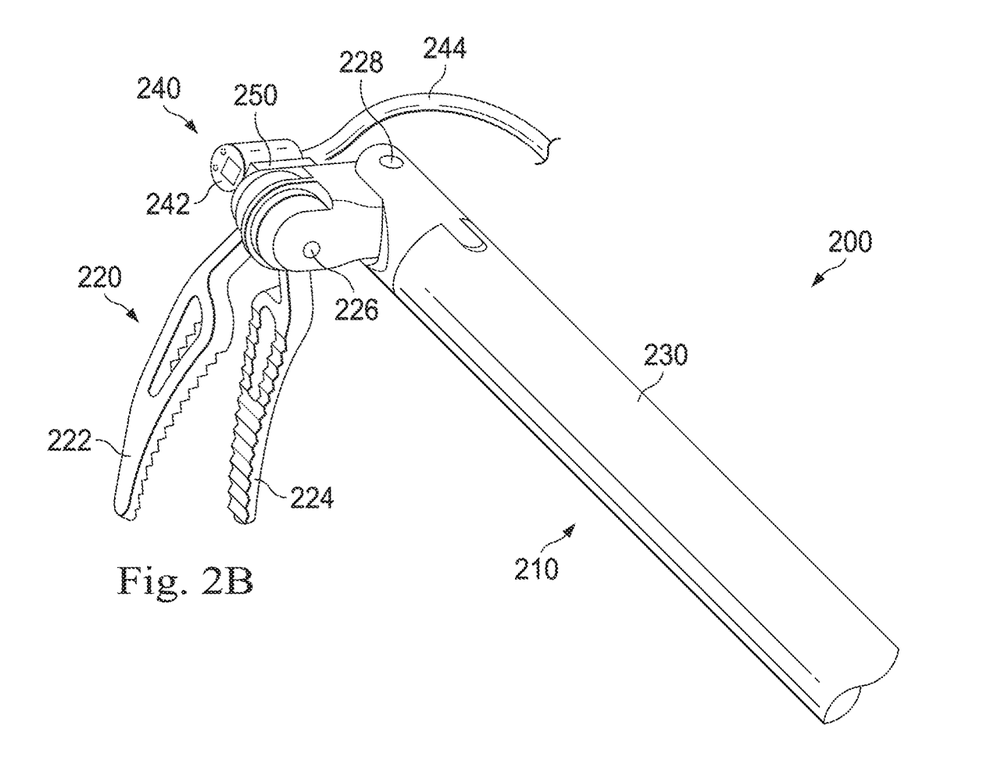

FIGS. 2A and 2B are simplified diagrams of a system 200 for providing on-demand functionality during a medical procedure according to some embodiments. According to some embodiments consistent with FIGS. 1A and 1B, system 200 may be incorporated into a teleoperational medical system, such as teleoperated medical system 10. For example, portions of system 200 may correspond to a surgical tool of a teleoperated medical system, such as surgical tool 28, and/or an accessory of a teleoperated medical system, such as accessory 19. In some examples, however, system 200 may be used independently of the teleoperated medical systems depicted in FIGS. 1A and 1B. For example, system 200 may be used in standalone and/or manually operated applications.

Instrument 210 includes an end effector 220 coupled to an instrument body 230. End effector 220 provides one or more functionalities to perform and/or assist in the performance of a medical procedure. According to some embodiments, end effector 220 may provide a surgical functionality such as gripping, extracting, cutting, injecting, stitching, stapling, ablating, delivering specific wavelengths of light for curing or reacting with other compounds, delivering liquids, chemicals, or drugs, providing surgical irrigation and suction and/or the like; a monitoring and/or diagnostic functionality such as imaging, sensing, probing, illuminating, and/or the like; and/or any number of other functionalities related to the medical procedure being performed. In some examples, end effector 220 may provide multiple functionalities. In the exemplary embodiment depicted in FIG. 2A, end effector 220 includes a pair of jaws 222 and 224 attached to an orthogonal pair of wrist joints 226 and 228 to provide a multi-directional gripping functionality.

Instrument body 230 is used for positioning, controlling, actuating, and/or communicating with end effector 220. According to some embodiments, instrument body 230 may include a rigid, flexible, and/or jointed shaft. The shaft may enclose one or more pull wires, power cables, communication cables, optical fibers, and/or the like to control, manipulate and/or communicate with end effector 220.

An accessory 240 is coupled to instrument 210 and provides one or more additional functionalities to perform and/or assist in the performance of the medical procedure. The additional functionalities provided by accessory 240 may generally include any of the functionalities listed previously with reference to end effector 220. In the exemplary embodiments depicted in FIGS. 2A and 2B, accessory 240 includes a camera 242. In some examples, camera 242 may include optical, electronic, and/or mechanical components such as an image sensor chip, lens, illumination fiber, and/or mechanical support members. Although camera 242 is depicted as a unidirectional, monocular camera, it is to be understood that camera 242 may include a plurality of imaging components for an expanded field of view and/or for binocular imaging, including three dimensional imaging. For example, camera 242 may include a 360 degree camera with back-to-back hemispherical lenses (which may be known as a hammerhead camera). Additionally or alternately, camera 242 may include a Raman spectroscopy probe, an optical coherence tomography (OCT) sensor, an ultrasound probe, and/or the like.

A flexible cable 244 is optionally coupled to camera 242 to provide electrical power, illumination energy, and/or data communication to camera 242. In some examples, flexible cable 244 may be omitted, such as when camera 242 includes an on-board battery and/or wireless communication capabilities, and/or when accessory 240 is otherwise functional as a freestanding attachment. The camera 242 or other accessory type 242 may receive power and/or transmit data through electrical contacts at the attachment point on the instrument body 228 or 230 and similarly, allow for the omission of the cable entirely or allow the cable to be smaller in diameter because some signal and/or data travel through the electrical contacts at the attachment point instead of through the cable.

The electrical contacts at the attachment point (if present) or other sensor types embedded inside the accessory 242 or inside the instrument shaft 230 (such as a hall effect magnetic field sensor or RFID receiver) point may also allow the instrument and software control system to detect status information about the accessory such as the identity, presence, alignment, and/or orientation of the accessory on the shaft. Based on the detected status information, the accessory may be monitored and/or the functionality of the accessory may be enabled or disabled. Sensors embedded in the accessory or shaft may also be used to detect status information such as a proper or improper coupling of the accessory to the shaft and enable or disable the accessory based on the detected condition. The detected accessory and functional capability of the accessory may also determine the user interface that is displayed to a user at the console 16 or at other display devices in the medical system 10. For example, a detected condition associated with an accessory that is a forward facing camera may present the user with a user interface that is different from a user interface presented if a reverse facing camera is the detected accessory. Similarly, different virtual control and gauges may be presented in the user interface based upon the detected accessory.

In FIG. 2A, camera 242 is depicted as being coupled to instrument 210 at a position near the base of end effector 220. In FIG. 2B, camera 242 depicted as being coupled between wrist joints 226 and 228. More generally, it is to be understood that camera 242 may be coupled to instrument 210 at any suitable position of end effector 220 and/or instrument body 230, including directly on jaws 222 and 224 (e.g., on the outer surface of jaw 222 such that jaws 222 and 224 retain their gripping functionality), and/or at any position along instrument body 230.

The one or more additional functionalities provided by accessory 240 augment the one or more functionalities provided by end effector 220. That is, the one or more additional functionalities provided by accessory 240 do not interfere with the one or more functionalities provided by end effector 220 in a substantial and/or mutually exclusive manner. For example, when end effector 220 provides a gripping functionality and accessory 240 provides an imaging functionality, each of these functionalities are concurrently available to system 200. This example is depicted in FIGS. 2A and 2B, where a camera 242 is coupled to end effector 220 in a manner and location that does not substantially interfere with the independent operation of jaws 222 and 224 and/or wrist joints 226 and 228. At most, jaws 222 and 224 may partially block the field of view of camera 242 and the range of motion of wrist joints 226 and 228 may be slightly reduced. Still, the multi-directional gripping functionality of end effector 220 and the imaging functionality of camera 242 remain substantially intact. By contrast, if camera 242 was held in the grasp of jaws 222 and 224 during operation, then the gripping functionality of jaws 222 and 224 would not remain intact because jaws 222 and 224 would not be usable for purposes other than holding camera 242. In addition to avoiding physical interference with end effector 220, accessory 240 may be functionally compatible with end effector 220. For example, accessory 240 may provide an imaging mode that is compatible with the surgical procedure being performed. The imaging mode may include, for instance, certain modes of ultrasound that are compatible with the surgical procedure but may exclude other modes of ultrasound that are incompatible.

In some examples, the additional functionalities provided by accessory 240 may be complementary to the functionalities of end effector 220, such that system 200 provides a complementary set of two or more functionalities. For example, end effector 220 may provide a surgical functionality (e.g., gripping, extracting, cutting, cauterizing, injecting, stitching, stapling, ablating, delivering specific wavelengths of light for curing or reacting with other compounds, delivering liquids, chemicals, and/or drugs, providing surgical irrigation and suction, and/or the like) and accessory 240 may provide a complementary monitoring and/or diagnostic functionality (e.g., imaging, sensing, probing, and/or the like). Consistent with such embodiments, an operator of system 200 may concurrently perform and monitor the medical procedure using the surgical functionality of end effector 220 and the complementary monitoring functionality of accessory 240, respectively. Other examples of end effectors and accessories that provide a complementary set of functionalities may include, but are not limited to: an endoscopic camera and an illumination source; a thermal ablation tool and a tissue temperature sensor; a fluorescent imager and an excitation source, and/or the like.

Because end effector 220 and accessory 240 are coupled, their relative position and orientation may be maintained during the medical procedure without continuous intervention (i.e., without independently maneuvering end effector 220 and accessory 240). Moreover, because there is little or no risk of collision, end effector 220 and accessory 240 may be positioned in close proximity to each other, enhancing the complementarity of their respective functionalities. For example, end effector 220 and accessory 240 may be directly coupled. Therefore, the multiple functionalities of end effector 220 and accessory 240 may generally be simpler to use and provide greater complementarity in comparison to alternative arrangements, such as an arrangement in which an accessory is attached to a separate instrument that is positioned independently of instrument 210 and does not move together with instrument 210.

In the exemplary embodiments depicted in FIGS. 2A and 2B, camera 242 provides an imaging functionality that is complementary to the gripping functionality of end effector 220. This complementary set of imaging and gripping functionalities may be used, for example, to visually monitor the operation of end effector 220 in an otherwise concealed and/or hard-to-see location. For example, camera 242 may be used to provide visual monitoring during the performance of Nissen fundoplication, a procedure in which stomach tissue is wrapped around the lower end of the esophagus and stitched into place. The tissue to be wrapped around the esophagus is obtained via circumferential dissection from the posterior of the esophagus, close to several major arteries and nerves. Whereas a conventional monitoring system may have difficulty monitoring the operation of end effector 220 during circumferential dissection (i.e., because the view is blocked by the esophagus), camera 242 may provide visual monitoring throughout the circumferential dissection due to the close proximity of camera 242 to end effector 220. Another illustrative application for system 200 may be partial nephrectomies, particularly cases with lateral and/or posterior tumors that are otherwise challenging to visually monitor from a conventional camera placement (e.g., an anterior port).

During a medical procedure, end effector 220 is positioned inside a patient body (e.g., in a body cavity), and instrument body 230 extends between end effector 220 and the outside of the patient body. For example, instrument body 230 may be attached to a teleoperated manipulator arm and/or may be manually controlled by a surgeon from outside the patient body. In some examples, the size of instrument body 230 may substantially match the size of an opening in the patient body through which instrument 210 extends. For example, instrument body 230 may extend through a cannula located at a patient body wall, and the internal diameter of the cannula may substantially match the outer diameter of instrument body 230. In such scenarios, it may be difficult and/or infeasible to insert instrument 210 into to patient body while accessory 240 is attached.

Moreover, it may not be desirable for accessory 240 to be coupled to instrument 210 continuously throughout a medical procedure. For example, the maneuverability of instrument 210 may be reduced when accessory 240 is attached, so it may be desirable to perform certain steps without accessory 240. In addition, it may be desirable to attach different accessories to instrument 210 at different times during the medical procedure without withdrawing and reinserting instrument 210 into the patient body. For example, it may be desired to monitor the procedure using a camera accessory at certain times and an ultrasound imager accessory at other times. Furthermore, it may be desirable to attach accessory 240 at different positions and/or at different orientations relative to instrument 210 at different times during the medical procedure. For example, it may be desired to orient a camera toward a distal end of instrument 210 when instrument 210 is being inserted into the patient body and toward a proximal end of instrument 210 when instrument 210 is being withdrawn to prevent collisions during insertion and withdrawal.

To address these challenges, accessory 240 is removably coupled to instrument 210. Consequently, accessory 240 may be attached and/or removed from instrument 210 while inside the patient body and/or during a medical procedure. In this regard, accessory 240 provides on-demand additional functionality that augments and/or complements the functionality of end effector 220 at certain times during the procedure, and which may be removed at other times without substantial disruption to the procedure.

A mount 250 is used to removably couple accessory 240 to instrument 210. In some examples, mount 250 may be fixedly attached to one or more of accessory 240 and instrument 210. For example, mount 250 may be fixedly attached to instrument 210 and may include a mechanism for removably coupling to accessory 240. Alternately or additionally, mount 250 may be fixedly attached to accessory 240 and may include a mechanism for removably coupling to instrument 210. In some examples, mount 250 may include two or more sub-components that are fixedly attached to each of instrument 210 and accessory 240, such as a male sub-component and a female sub-component that may be removably mated. In some examples, mount 250 may not be fixedly attached to either accessory 240 or instrument 210, and may instead include a standalone binding mechanism such as a strap and/or a clamp.

Mount 250 may provide one or more of a variety of connection types between accessory 240 and instrument 210, including rigid, flexible, moveable, slideable, and/or pivoted connections. In some examples, mount 250 may enforce a specific position and/or orientation of accessory 240 relative to instrument 210. For example, mount 250 may force a camera accessory to align axially along instrument body 220. To illustrate, accessory 240 and instrument 210 may each include magnets with fixed polarities that cause accessory 240 and instrument 210 to align in the same way each time they are coupled. Additionally or alternately, mount 250 may support a range of relative positions and/or orientations.

The mechanism used by mount 250 for removable coupling may include a mechanical mechanism such as a clip, tab, clamp, screw, strap, and/or latch; a magnetic mechanism such as a permanent magnet and/or an electromagnet; a chemical mechanism such as a temporary glue and/or a pressure-sensitive adhesive; and/or the like and/or any combination thereof. In the illustrative embodiments depicted in FIGS. 2A and 2B, mount 250 is attached to accessory 240 and includes a magnet that removably couples to end effector 220 when accessory 240 is placed near end effector 220. Although mount 250 is depicted as protruding from the side of accessory 240, it is to be understood that mount 250 may be incorporated, embedded, and/or otherwise integrated into accessory 240 and/or instrument 210. In some examples, end effector 220 may be constructed using a magnetic material such as 416 stainless steel and/or may have a magnetic material embedded inside to ensure that mount 250 couples to end effector 220.

In addition to providing a mechanism to removably couple accessory 240 to instrument 210, mount 250 may optionally provide one or more additional power, data, and/or control connections (e.g., electrical, optical, and/or mechanical connections) between accessory 240 and instrument 210. For example, the additional connections may enable an operator to control accessory 240 and/or receive data signals from accessory 240 from outside the patient body via instrument 210.

A variety of techniques may be used to couple and/or remove accessory 240 to and from instrument 210. These include but are not limited to techniques that use one or more second instruments, self-service techniques, and/or techniques that use a specialized cannula. In some examples, one or more second instrument (e.g., forceps, graspers, a surgical bulldog clamp, a magnet, and/or the like) may be used to place accessory 240 in an appropriate position and/or orientation relative to instrument 210 to engage the coupling mechanism of mount 250. Consistent with such embodiments, accessory 240 may include one or more protrusions and/or notches (e.g., a flange, tab, handle, and/or the like) to facilitate being picked up and moved by the one or more second instruments. In some examples, the one or more second instruments may further be used fasten accessory 240 to instrument 210, as appropriate based on the coupling mechanism of mount 250. For example, the one or more second instruments may be used to tie, strap, screw, and/or latch accessory 240 to instrument 210. In some examples, instrument 210 may be capable of self-service (i.e., using its own functionalities to attach accessory 240 to itself). For example, end effector 220 may be used to grasp accessory 240 and reach backward to couple accessory 240 to instrument 210. After accessory 240 is coupled to instrument 210, end effector 220 may release its grip on accessory 240 and resume its normal functionality. In further examples, a fixture such as a cannula may be adapted to couple accessory 240 to instrument 210. Examples of cannulas adapted to couple accessory 240 to instrument 210 are described below with reference to FIGS. 5A and 5B When accessory 240 is not coupled to instrument 210, accessory 240 is generally positioned so as not to interfere with the ongoing medical procedure. In some examples, accessory 240 may be withdrawn from the patient body, parked in a predetermined site within the patient body, left dangling or free-floating in the patient body, moved to a different instrument and/or a different location on the same instrument, and/or the like. For example, accessory 240 may be parked (e.g., clipped and/or magnetically coupled) to a cannula, a body wall, the peritoneum, patient organs, and/or the like. In an illustrative embodiment, accessory 240 may be parked against an internal surface of the patient's body wall using a magnet located outside the patient body on the opposite side of the body wall. In another example, accessory 240 may be parked to the peritoneum using an atraumatic grasper and/or a reusable clamp, such as a bulldog clamp. In some examples, accessory 240 may be held and/or used by a second instrument when not being used by instrument 210. In some examples, accessory 240 may be moved and/or slid up to a proximal portion of instrument 210 when not in use so as not to interfere with operations occurring at the distal end of instrument 210. While parked, accessory 240 may enter an idle state and/or may continue to provide functionality, such as providing continuous visual monitoring of the medical procedure from the viewpoint of the parking site.

Figure 3A:
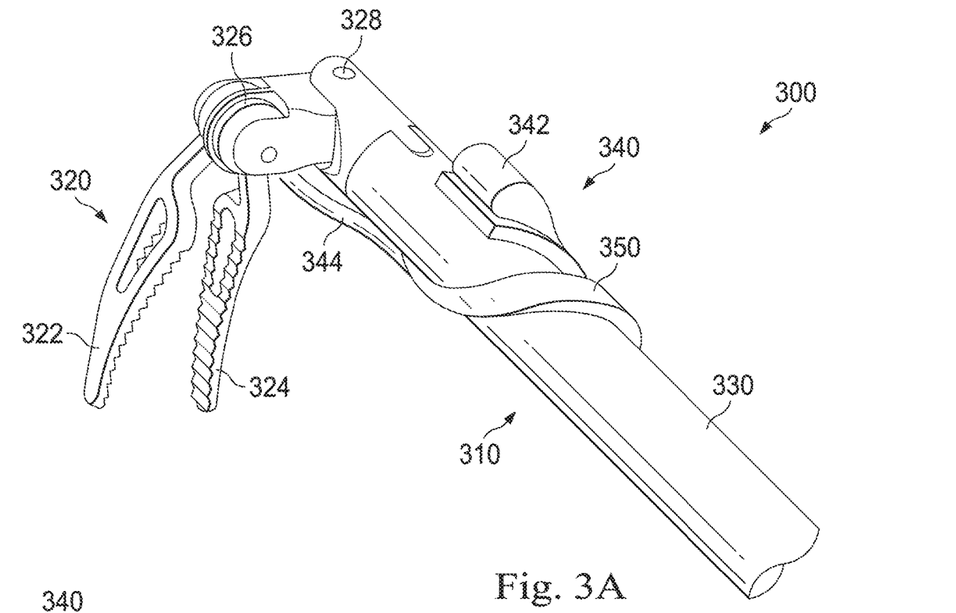
FIGS. 3A-3C are simplified illustrations of a system with a clip-mounted accessory according to some embodiments.
Figure 3B:
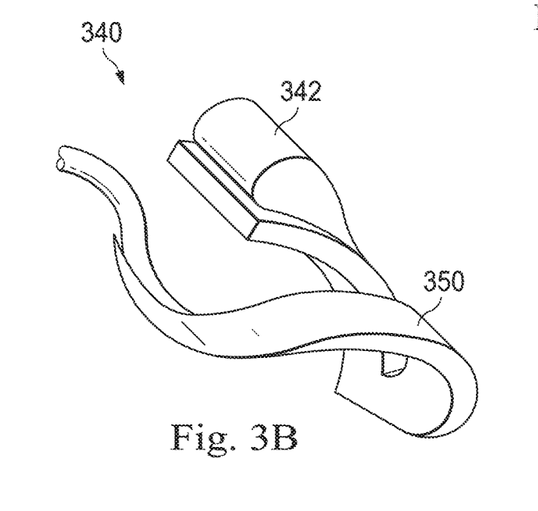
Figure 3C:
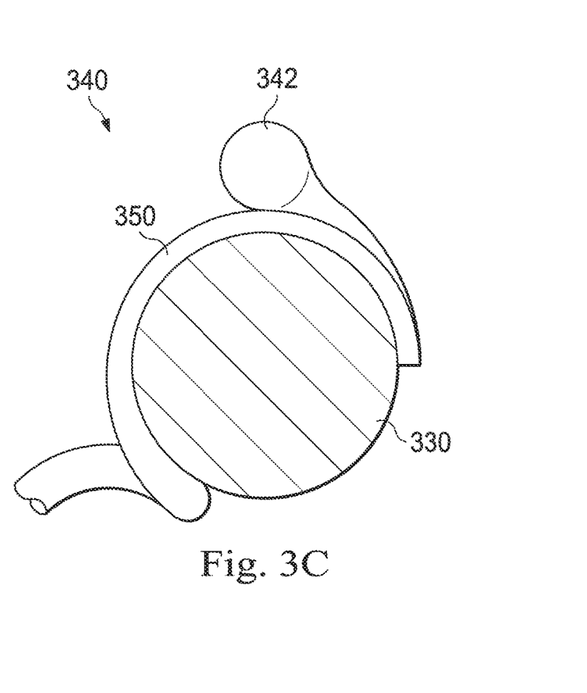

FIGS. 3A-3C are simplified illustrations of a system 300 with a clip-mounted accessory according to some embodiments. As depicted in FIGS. 3A-3C, system 300 includes an instrument 310, instrument body 330, accessory 340, and mount 350. These features generally correspond to similarly-labeled features described above with respect to FIGS. 2A and 2B. In the exemplary embodiments depicted in FIGS. 3A-3C, end effector 320 includes jaws 322 and 324 and wrist joints 326 and 328, and accessory 340 includes a camera 342 attached to a flexible cable 344.

Unlike FIGS. 2A and 2B, which depict mount 250 as providing a magnetic coupling mechanism, FIGS. 3A-3C depict mount 350 as a molded clip that extends between camera 342 and flexible cable 344 and partially wraps around and conforms to the outer shaft of instrument body 330. The molded clip may be formed using a semi-rigid material, such as a suitable polymer material, that snaps into place around instrument body 330. To the extent that electrical and/or optical cables run through flexible cable 344, those cables may extend through the molded clip to reach camera 342. In some examples, the molded clip may be fitted to a standard instrument shaft size. Accordingly, accessory 340 may be removably coupled to a variety of existing instruments that use the standard shaft size without modification to the existing instruments.

Figure 4:
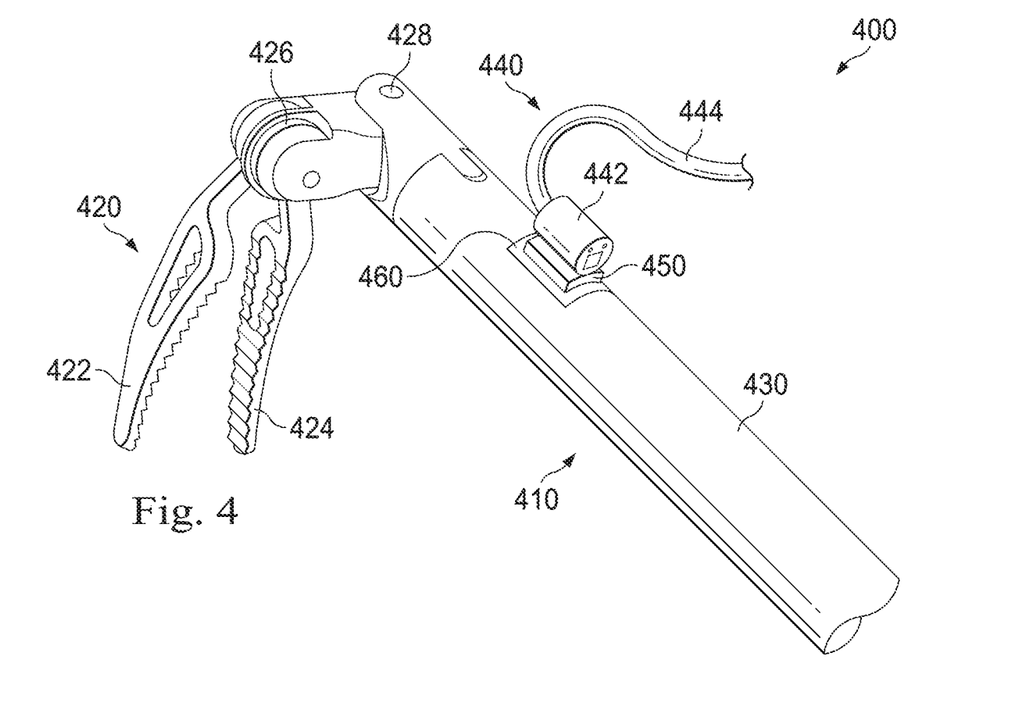
FIG. 4 is a simplified illustration of a system with a camera accessory that provides a proximal camera view according to some embodiments.

FIG. 4 is a simplified illustration of a system 400 with a camera accessory that provides a proximal camera view (i.e., a view toward the proximal end of the instrument) according to some embodiments. As depicted in FIG. 4, system 400 includes an instrument 410, end effector 420, instrument body 430, accessory 440, and mount 450. These features generally correspond to similarly-labeled features described above with respect to FIGS. 2A-3C. In the exemplary embodiments depicted in FIG. 4, end effector 420 includes jaws 422 and 424 and wrist joints 426 and 428, and accessory 440 includes a camera 442 attached to a flexible cable 444. In this example, mount 450 is a magnetic mount fixedly attached to accessory 440.

Instrument 410 optionally includes a metallic and/or magnetic plate 460 attached to instrument body 430. Plate 460 allows magnetic mount 450 to couple to otherwise non-metallic and/or non-magnetic portions of instrument 410, such as the polymer or composite shaft of the instrument body 430. Plate 460 is generally selected to be thin and/or conformal to instrument body 430 so as to minimize the impact of plate 460 on the operation of instrument 410. Although a single plate is depicted in FIG. 4, it is to be understood that instrument 410 may include a plurality of plates at a plurality of locations where it is desired to attach accessory 440.

Unlike FIGS. 2A and 2B, which depict camera 242 as providing a distal camera view of instrument 210 (i.e., a view towards end effector 420), FIG. 4 depicts camera 442 as providing a proximal camera view of instrument 410. In this orientation, camera 442 provides visual monitoring along the shaft of instrument body 430 towards the cannula through which instrument 410 is inserted. When withdrawing instrument 410 from the patient body, the proximal camera view helps to monitor the location of the ureter, arteries, nerves, and/or other sensitive tissue to ensure that they are not damaged as instrument 410 exits the body.

When accessory 440 is used to provide visual monitoring during the insertion and withdrawal of one or more instruments through a cannula (and/or in various other applications), it may be desired to automatically remove accessory 440 from a first instrument when it is withdrawn from the patient body. Additionally, it may be desired to automatically couple accessory 440 to the next instrument that is inserted through the cannula (which may be the same or different than the first instrument). In the interim, it may be desired to flip the orientation of accessory 440 because a proximal camera view is used during withdrawal, whereas a distal camera view is used during insertion. Accordingly, the cannula may be adapted to automatically remove, park, flip, and/or couple accessory 440 as one or more instruments pass through the cannula, as described in further detail below.

Figure 5A:
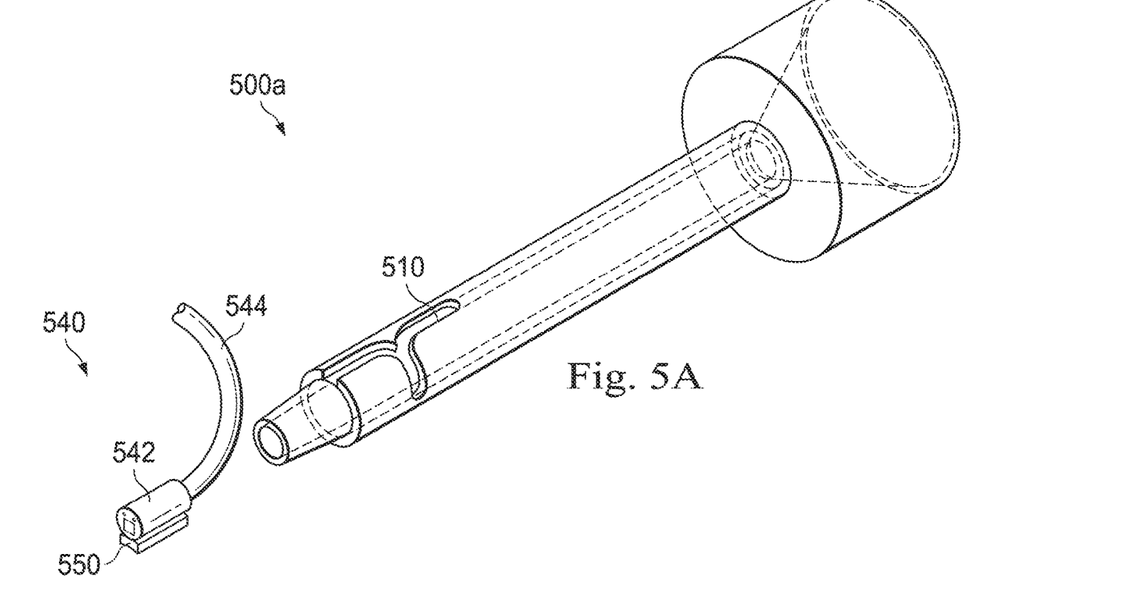
FIGS. 5A and 5B are simplified diagrams of cannulas adapted to automate accessory management according to some embodiments.
Figure 5B:
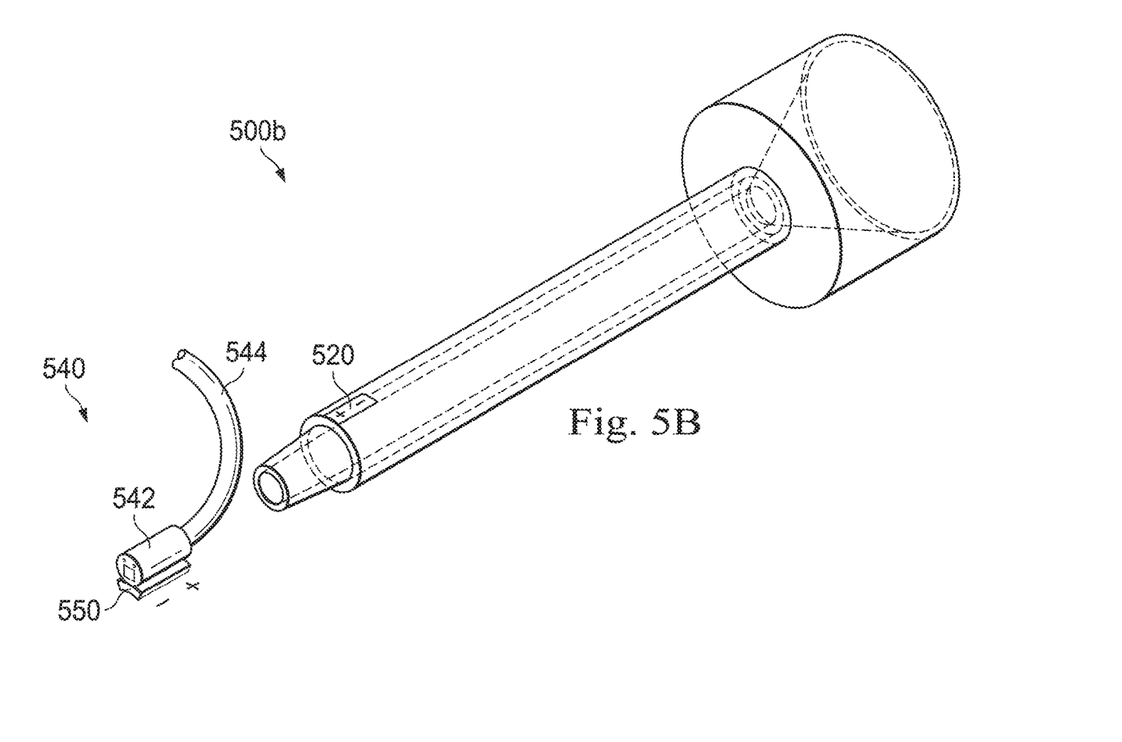

FIGS. 5A and 5B are simplified diagrams of cannulas 500a and 500b adapted to automate accessory management according to some embodiments. According to some embodiments consistent with FIGS. 2A-4, cannulas 500a and 500b may be configured to manage an accessory 540 coupled to a mount 550. Accessory 540 and mount 550 generally correspond to similarly-labeled features of FIGS. 2A-4.

Cannula 500a includes a mechanical groove 510 to automatically remove, park, flip, and/or couple accessory 540 as one or more instruments pass through cannula 500a. Groove 510 may include one or more protrusions and/or notches that are shaped to guide accessory 540 along a predetermined trajectory when an instrument (not shown) is withdrawn and/or inserted through cannula 500a. More specifically, groove 510 is designed to flip the orientation of accessory 540 each time an instrument is withdrawn, such that accessory 540 provides a distal camera view during insertion and a proximal camera view during withdrawal. Moreover, groove 510 is designed to maintain accessory 540 in a parked position when there is no instrument in cannula 500a.

Similarly, cannula 500b is adapted to automatically remove, park, flip, and/or couple accessory 540 as one or more instruments pass through cannula 500a. Cannula 500b is particularly suited for embodiments in which mount 550 is a magnetic mount. Cannula 500b includes a cannula magnet 520 that is appended to and/or incorporated into cannula 500b. Like mechanical groove 510, cannula magnet 520 exerts a force on magnetic mount 550 to flip the orientation of accessory 540 each time an instrument is withdrawn. For example, cannula magnet 540 may be oriented relative to magnetic mount 550 such that accessory 540 provides a distal camera view during insertion and a proximal camera view during withdrawal. Moreover, cannula magnet 520 may magnetically couple to magnetic mount 550 to maintain accessory 540 in a parked position when there is no instrument in cannula 500b.

In some examples, a hybrid cannula may incorporate a mechanical groove, such as mechanical groove 510, and a cannula magnet, such as cannula magnet 520. The hybrid cannula may be used to increase the amount of physical control of the cannula over an accessory and/or may be used to achieve compatibility with accessories having both magnetic and non-magnetic mounts.

To the extent that the examples depicted in FIGS. 5A and 5B may automate the process of flipping accessory 540 in one direction (e.g., from a proximal camera view to a distal camera view), another mechanism may be used to flip accessory 540 in the opposite direction (e.g., from distal to proximal). For example, a second instrument may be used to manually change the orientation of accessory 540 from a distal to proximal camera view prior to withdrawing the host instrument through cannula 500a or 500b.

Figure 6:
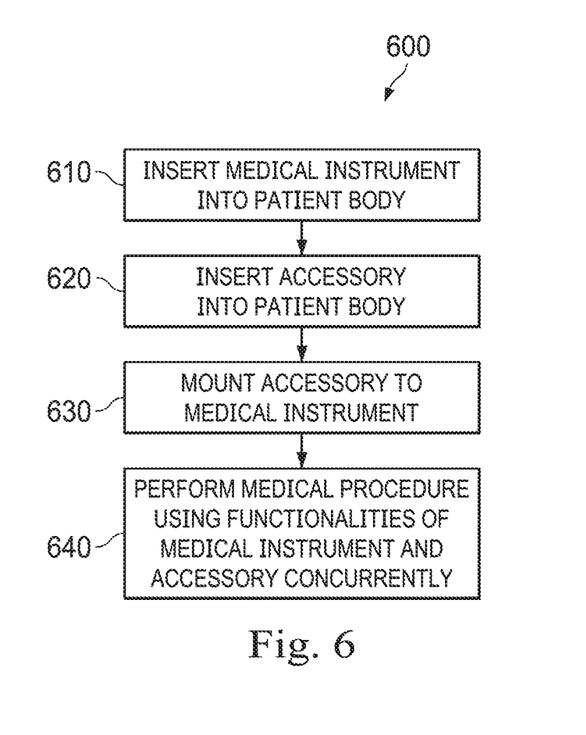
FIG. 6 is a simplified diagram of a method for providing on-demand functionality during a medical procedure according to some embodiments.

FIG. 6 is a simplified diagram of a method 600 for providing on-demand functionality during a medical procedure according to some embodiments. According to some embodiments consistent with FIGS. 2A-5B, method 600 may be performed using a system configured to provide on-demand functionality during a medical procedure according, such as system 200.

At a process 610, a medical instrument, such as instrument 210, is inserted into a patient body. The medical instrument provides one or more functionalities applicable to the medical procedure. For example, the medical instrument may include an end effector, such as end effector 220. According to some examples, the medical instrument may be inserted into the patient body through a cannula, such as cannula 500a and/or 500b.

At a process 620, an accessory, such as accessory 240, is inserted into the patient body. The accessory provides one or more additional functionalities that augment the one or more functionalities of the medical instrument. In some examples, the accessory may be inserted into the patient body through a different opening in the patient body and/or a different cannula than the medical instrument. In some examples, the accessory may be inserted through the same opening in the patient body as the medical instrument. For example, the medical instrument may be inserted through a cannula that includes a reducer, which forms a gap between levels of the reducer. Consistent with such examples, the accessory may be inserted through the gap in the reducer. To facilitate insertion through an irregular opening (e.g., a non-circular opening such as the gap of the cannula reducer), one or more features of the accessory may be adapted to fit through the irregular opening. For example, a cable attached to the accessory may be formed as a flat cable rather than a circular cable.

At a process 630, the accessory is mounted to the medical instrument. In some examples, the accessory may be coupled using a mounting device, such as mount 250. A variety of techniques may be employed for engaging and/or disengaging the coupling mechanism between the accessory and the medical instrument, as discussed previously with reference to FIG. 2. In some examples, the accessory may be parked to the cannula through which the medical instrument is inserted, and may automatically couple to the medical instrument as the medical instrument is inserted through the cannula and/or decouple from the medical instrument as the medical instrument is withdrawn through the cannula.

At a process 640, a medical procedure is performed using the functionality of the medical instrument and the additional functionality of the accessory concurrently. The medical procedure may include virtually any type of procedure in which two or more functionalities are used at the same time. In some examples, performing the medical procedure may include performing a surgical operation using the medical instrument (e.g., gripping, cutting, injecting, stitching, cauterizing, and/or the like) and concurrently monitoring the performance of the physical using the accessory (e.g., imaging, temperature sensing, and/or the like). In some examples, performing the medical procedure may include imaging a scene inside the patient body using the medical instrument and concurrently illuminating the scene using the accessory.

Some examples of processors may include non-transient, tangible, machine readable media that include executable code that when run by one or more processors may cause the one or more processors to perform the processes of method 600. Some common forms of machine readable media that may include the processes of method 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system for providing on-demand functionality during a medical procedure comprising:
    a first instrument comprising an instrument body and an end effector, the end effector providing a first functionality;
    a first accessory providing a second functionality; and
    a mounting device comprising:
        a first mounting component attached to the first accessory; and
        a second mounting component integrated in the first instrument, the second mounting component including a groove,
        wherein the first mounting component is decouplable from the second mounting component, and wherein the first mounting component is configured to interact with the second mounting component to removably couple the first accessory to the first instrument to augment the first functionality with the second functionality,
        wherein the mounting device is configured to transition the first accessory between a first configuration and a second configuration while both the first accessory and the end effector are inside a patient body as the first mounting component is received by and moves within the groove of the second mounting component,
        wherein in the first configuration, the first accessory is in a distal-facing orientation relative to the first instrument, and
        wherein in the second configuration, the first accessory is in a proximal-facing orientation relative to the first instrument.

2. The system of claim 1, wherein the first or second functionality includes a surgical functionality.

3. The system of claim 1, wherein the first or second functionality includes a monitoring functionality.

4. The system of claim 1, wherein the first or second functionality is selected from a group consisting of gripping, extracting, cutting, injecting, stitching, stapling, ablating, delivering light, delivering liquids, providing irrigation, or providing suction.

5. The system of claim 1, wherein the first or second functionality is selected from a group consisting of imaging, sensing, probing, or illuminating.

6. The system of claim 1, wherein the first functionality includes a surgical functionality and the second functionality includes a complementary monitoring functionality.

7. The system of claim 1, wherein the first functionality includes an imaging functionality and the second functionality includes a complementary illumination functionality.

8. The system of claim 1, wherein the first accessory includes a camera.

9. The system of claim 1, wherein the first accessory provides a distal camera view when the first instrument is inserted into the patient body and a proximal camera view when the first instrument is withdrawn from the patient body.

10. The system of claim 1, wherein the first accessory includes a protrusion or a notch to facilitate being picked up by a second instrument.

11. The system of claim 1, wherein the first accessory is configured to be parked inside the patient body when not attached to the first instrument.

12. The system of claim 11, wherein the first accessory is configured to be parked against a body wall of the patient body using a magnet positioned outside the patient body opposite the first accessory.

13. The system of claim 11, wherein the first accessory continues to provide the second functionality while parked.

14. The system of claim 1, wherein the first accessory is couplable to the end effector of the first instrument.

15. The system of claim 1, wherein the first accessory is couplable to a distal end of the instrument body of the first instrument.

16. The system of claim 1, wherein the first mounting component is fixed to the first accessory such that an orientation of the first mounting component relative to the first instrument changes when the orientation of the first accessory changes relative to the first instrument.

17. A system for providing on-demand functionality during a medical procedure comprising:
    an instrument comprising an instrument body and an end effector, the end effector providing a first functionality;
    an accessory providing a second functionality; and
    a mounting device comprising:
        a first mounting component attached to the accessory, the first mounting component including a first magnet having a first polarity; and
        a second mounting component integrated in the instrument, the second mounting component including a second magnet having a second polarity different from the first polarity,
        wherein the first mounting component is decouplable from the second mounting component, and wherein the first mounting component is configured to interact with the second mounting component to removably couple the accessory to the instrument to augment the first functionality with the second functionality,
        wherein the mounting device is configured to transition the accessory between a first configuration and a second configuration while both the accessory and the end effector are inside a patient body based on an interaction between the first polarity of the first magnet and the second polarity of the second magnet, wherein in the first configuration, the accessory is in a distal-facing orientation relative to the instrument, and wherein in the second configuration, the accessory is in a proximal-facing orientation relative to the instrument.

18. The system of claim 17, wherein the first functionality includes a surgical functionality and the second functionality includes a complementary monitoring functionality.

19. The system of claim 17, wherein the first functionality includes an imaging functionality and the second functionality includes a complementary illumination functionality.

20. The system of claim 17, wherein the accessory provides a distal camera view when the instrument is inserted into the patient body and a proximal camera view when the instrument is withdrawn from the patient body.

* * * * *